US00PP31778P2

(12) United States Plant Patent
Wain

(10) Patent No.: US PP31,778 P2
(45) Date of Patent: May 19, 2020

(54) ***CHRYSANTHEMUM* PLANT NAMED 'DOCHRYSBUMB'**

(50) Latin Name: ***Chrysanthemum* X *morifolium***
Varietal Denomination: Dochrysbumb

(71) Applicant: DUMMEN GROUP B.V., De Lier (NL)

(72) Inventor: Peter Wain, Locks Heath (GB)

(73) Assignee: Dümmen Group B.V., De Lier (NL)

( * ) Notice: Subject to any disclaimer, the term of this patent is extended or adjusted under 35 U.S.C. 154(b) by 0 days.

(21) Appl. No.: 16/501,551

(22) Filed: Apr. 29, 2019

(51) Int. Cl.
*A01H 5/02* (2018.01)
*A01H 6/14* (2018.01)

(52) U.S. Cl.
USPC ..... Plt./289

(58) Field of Classification Search
USPC ..... Plt./289
CPC ..... A01H 5/02; A01H 5/0255; A01H 6/14; A01H 6/1424
See application file for complete search history.

*Primary Examiner* — June Hwu
(74) *Attorney, Agent, or Firm* — C. A. Whealy

(57) ABSTRACT

A new and distinct cultivar of *Chrysanthemum* plant named 'Dochrysbumb', characterized by its upright to somewhat outwardly spreading and uniformly and mounded plant habit; moderately vigorous growth habit; freely branching habit; dense and full plant form; uniform and freely flowering habit; medium-sized to large decorative-type inflorescences with dark yellow-colored ray florets; freely and early flower habit; and good postproduction longevity.

2 Drawing Sheets

Botanical designation: *Chrysanthemum* X *morifolium*.
Cultivar denomination: 'DOCHRYSBUMB'.

BACKGROUND OF THE INVENTION

The present invention relates to a new and distinct *Chrysanthemum* plant, botanically known as *Chrysanthemum* X *morifolium*, commercially grown as a potted *Chrysanthemum* plant and hereinafter referred to by the name 'Dochrysbumb'.

The new *Chrysanthemum* plant is a product of a planned breeding program conducted by the Inventor in Fareham, Hampshire, United Kingdom. The objective of the breeding program is to create new potted *Chrysanthemum* plants with numerous attractive inflorescences.

The new *Chrysanthemum* plant originated from a cross-pollination made in January, 2014 by the Inventor in Fareham, Hampshire, United Kingdom of a proprietary selection of *Chrysanthemum* X *morifolium* identified as code number 807825, not patented, as the female, or seed, parent with a proprietary selection of *Chrysanthemum* X *morifolium* identified as code number 807744, not patented, as the male, or pollen, parent. The new *Chrysanthemum* plant was discovered and selected by the Inventor as a single flowering plant from within the progeny of the stated cross-pollination in a controlled greenhouse environment in Fareham, Hampshire, United Kingdom in September, 2014.

Asexual reproduction of the new *Chrysanthemum* plant by terminal vegetative cuttings was first conducted in Fareham, Hampshire, United Kingdom in December, 2014. Asexual reproduction by terminal vegetative cuttings has shown that the unique features of this new *Chrysanthemum* plant are stable and reproduced true to type in successive generations.

SUMMARY OF THE INVENTION

Plants of the new *Chrysanthemum* have not been observed under all possible combinations of environmental conditions and cultural practices. The phenotype may vary somewhat with variations in environmental conditions such as temperature, daylength and light intensity, without, however, any variance in genotype.

The following traits have been repeatedly observed and are determined to be the unique characteristics of 'Dochrysbumb'. These characteristics in combination distinguish 'Dochrysbumb' as a new and distinct *Chrysanthemum* plant:

1. Upright to somewhat outwardly spreading and uniformly and mounded plant habit.
2. Moderately vigorous growth habit.
3. Freely branching habit; dense and full plant form.
4. Uniform and freely flowering habit.
5. Medium-sized to large decorative-type inflorescences with dark yellow-colored ray florets.
6. Freely and early flower habit.
7. Good postproduction longevity.

Plants of the new *Chrysanthemum* can be compared to plants of the female parent selection. Plants of the new *Chrysanthemum* differ primarily from plants of the female parent selection in the following characteristics:

1. Plants of the new *Chrysanthemum* have larger inflorescences than plants of the female parent selection.
2. Ray florets of plants of the new *Chrysanthemum* are darker yellow in color than ray florets of plants of the female parent selection.

Plants of the new *Chrysanthemum* can be compared to plants of the male parent selection. Plants of the new *Chrysanthemum* differ primarily from plants of the male parent selection in the following characteristics:

1. Plants of the new *Chrysanthemum* are taller than plants of the male parent selection.
2. Plants of the new *Chrysanthemum* and the male parent selection differ in ray floret color as plants of the new *Chrysanthemum* have inflorescences with dark yellow-colored ray florets whereas plants of the male parent selection have inflorescences with bronze-colored ray florets.

Plants of the new *Chrysanthemum* can also be compared to plants of *Chrysanthemum* X *morifolium* 'Fichrysun', not patented. In side-by-side comparisons, plants of the new *Chrysanthemum* differ primarily from plants of 'Fichrysun' in the following characteristics:

1. Plants of the new *Chrysanthemum* flower earlier than plants of 'Fichrysun'.
2. Plants of the new *Chrysanthemum* have larger inflorescences than plants of 'Fichrysun'.

BRIEF DESCRIPTION OF THE PHOTOGRAPHS

The accompanying photographs illustrate the overall appearance of the new *Chrysanthemum* plant showing the colors as true as it is reasonably possible to obtain in colored reproductions of this type. Colors in the photographs may differ slightly from the color values cited in the detailed botanical description which accurately describe the colors of the new *Chrysanthemum* plant.

The photograph on the first sheet is a side perspective view of a typical flowering plant of 'Dochrysbumb' grown in a container.

The photograph on the second sheet is a close-up view of a typical flowering plant of 'Dochrysbumb'.

DETAILED BOTANICAL DESCRIPTION

The aforementioned photograph and following observations and measurements describe plants grown during the spring in 15.25-cm containers in a polyethylene-covered greenhouse in Encinitas, Calif. and under cultural practices typical of commercial potted *Chrysanthemum* production. During the production of the plants, day temperatures averaged 26° C., night temperatures averaged 20° C. and light levels averaged 4,500 lux. Plants were propagated under long day/short night conditions and then grown under short day/long night conditions to induce inflorescence initiation and development. Plants were disbudded. Five plants were grown per pot and plants were 14 weeks old when the photographs and detailed description were taken. In the following description, color references are made to The Royal Horticultural Society Colour Chart, 2015 Sixth Edition, except where general terms of ordinary dictionary significance are used.

Botanical classification: *Chrysanthemum* X *morifolium* 'Dochrysbumb'.

Parentage:

*Female, or seed, parent.*—Proprietary selection of *Chrysanthemum* X *morifolium* identified as code number 807825, not patented.

*Male, or pollen, parent.*—Proprietary selection of *Chrysanthemum* X *morifolium* identified as code number 807744, not patented.

Propagation:

*Type.*—Terminal vegetative cuttings.

*Time to initiate roots, summer.*—About ten days at temperatures about 21° C.

*Time to initiate roots, winter.*—About twelve days at temperatures about 21° C.

*Time to produce a rooted young plant, summer.*—About three weeks at temperatures about 21° C.

*Time to produce a rooted young plant, winter.*—About four weeks at temperatures about 21° C.

*Root description.*—Medium in thickness, fibrous; typically light brown in color, actual color of the roots is dependent on substrate composition, water quality, fertilizer type and formulation, substrate temperature and physiological age of roots.

*Rooting habit.*—Freely branching; medium density.

Plant description:

*Plant and growth habit.*—Herbaceous decorative-type potted *Chrysanthemum*; stems upright to somewhat outwardly spreading giving a uniformly mounded appearance to the plant; numerous lateral branches and relatively short internodes, dense and full plant form; inverted triangle in overall plant shape; moderately vigorous growth habit and medium growth rate.

*Plant height.*—About 23.5 cm.

*Plant width.*—About 36 cm.

*Stem diameter, at the soil level.*—About 8 mm.

*Branching habit.*—Freely branching habit; about five to seven lateral branches develop after removal of terminal apex (pinching).

*Lateral branches.*—Length: About 17 cm. Diameter: About 4.5 mm. Internode length: Proximally, about 1.75 cm. Strength: Strong. Aspect: Upright to about 30° to 35° from vertical. Texture and luster: Moderately pubescence; moderately glossy. Color: Close to 146A.

Leaf description:

*Arrangement.*—Alternate, simple.

*Length, including petiole.*—About 9.5 cm.

*Width.*—About 5.25 cm.

*Shape.*—Palmately-lobed; roughly ovate in overall outline with three to five lobes.

*Apex.*—Cuspidate.

*Base.*—Attenuate.

*Margin.*—Broadly serrate and palmately lobed; sinuses between lateral lobes mostly divergent and medium to deep.

*Texture and luster, upper surface.*—Smooth, glabrous; moderately glossy.

*Texture and luster, lower surface.*—Sparsely pubescent; prominent venation; slightly glossy.

*Venation pattern.*—Palmate.

*Color.*—Developing and fully expanded leaves, upper surface: Darker than 147A; venation, close to 147A. Developing and fully expanded leaves, lower surface: Close to 147A; venation, close to 146A.

*Petioles.*—Length: About 3 cm. Diameter, proximally: About 3 mm by 2 mm. Texture and luster, upper surface: Smooth, glabrous; moderately glossy. Texture, lower surface: Sparsely pubescent; moderately glossy. Color, upper surface: Close to 146A. Color, lower surface: Close to 146A to 146B.

Inflorescence description:

*Form and flowering habit.*—Medium-sized to large decorative-type inflorescence form with obovate-shaped ray florets; inflorescences borne on terminals above and beyond the foliar plane; disc and ray florets arranged acropetally on a capitulum; freely flowering habit with about four to five inflorescences developing per lateral branch; inflorescences face mostly upright to somewhat outwardly.

*Fragrance.*—Mildly fragrant; pungent, herbaceous.

*Flowering response.*—Early flowering habit, plants exposed to natural season conditions begin flowering about seven weeks after start of photoinductive treatments.

*Inflorescence longevity.*—Inflorescences maintain good color and substance for about three to five weeks on the plant; inflorescences persistent.

*Inflorescence buds.*—Height: About 7 mm. Diameter: About 8 mm. Shape: Spherical. Color: Close to 147A.

*Inflorescence diameter.*—About 7 cm.

*Inflorescence height.*—About 2.2 cm.

*Disc diameter.*—About 5 mm, inconspicuous.

*Receptacles: Height: About* 6 mm. Diameter: About 6 mm. Shape: Rounded. Color: Close to 144A to 144B.

*Ray florets.*—Number of ray florets per inflorescence: About 178 arranged in numerous whorls. Orientation: Initially upright, then horizontal with development. Length: About 3.4 cm. Width: About 9 mm. Shape: Obovate; lower 33% to 50% fused. Apex: Obtuse. Base: Fused into a slender tube. Margin: Entire. Texture and luster, upper surface: Smooth, glabrous; velvety; slightly glossy. Texture and luster, lower surface: Smooth, glabrous; matte. Color: When opening and fully opened, upper surface: Close to 6A; venation, similar to lamina; color does not change with development. When opening and fully opened, lower surface: Close to 6C; towards the base, close to 144A and at the base, close to NN155D; venation, similar to lamina; color does not change with development.

*Disc florets.*—Number of disc florets per inflorescence: About 15 to 20 massed at the center of the receptacle; inconspicuous. Length: About 5 mm. Diameter, distally: About 1.5 mm. Shape: Tubular, elongated; apices, acute. Texture and luster, inner and outer surfaces: Smooth, glabrous; slightly glossy. Color, when opening and fully opened: Apex: Close to 9A. Mid-section: Close to 154D. Base: Close to NN155D.

*Phyllaries.*—Number of phyllaries per inflorescence: About 24 arranged in about three whorls. Length: About 1.1 cm. Width: About 4 mm. Shape: Lanceolate. Apex: Acuminate. Base: Truncate. Margin: Entire; membraneous and translucent. Texture and luster, upper surface: Smooth, glabrous; waxy; glossy. Texture and luster, lower surface: Densely pubescent; slightly glossy. Color, upper surface: Close to 146A. Color, lower surface: Close to 147A.

*Peduncles.*—Length, uppermost peduncle: About 4.4 cm. Diameter, uppermost peduncle: About 2 mm. Length, fourth peduncle: About 6.2 cm. Diameter, fourth peduncle: About 2 mm. Angle: About 30° to 40° from lateral branch axis. Strength: Strong; flexible. Texture and luster: Moderately pubescent; moderately glossy. Color: Close to 146A.

*Reproductive organs.*—Androecium: None observed. Gynoecium: Present only on ray florets. Pistil length: About 7 mm. Stigma shape: Bi-parted. Stigma color: Close to 6A. Style length: About 6 mm. Style color: Close to 6C. Ovary color: Close to 144A to 144B.

*Seeds and fruits.*—To date, seed and fruit production has not been observed on plants of the new *Chrysanthemum.*

Pathogen & pest resistance: To date, resistance to pathogens and pests common to *Chrysanthemum* plants has not been observed on plants of the new *Chrysanthemum.*

Garden performance: Plants of the new *Chrysanthemum* have demonstrated good garden performance and to tolerate temperatures from about 0° C. to about 35° C.

It is claimed:

1. A new and distinct *Chrysanthemum* plant named 'Dochrysbumb' as illustrated and described.

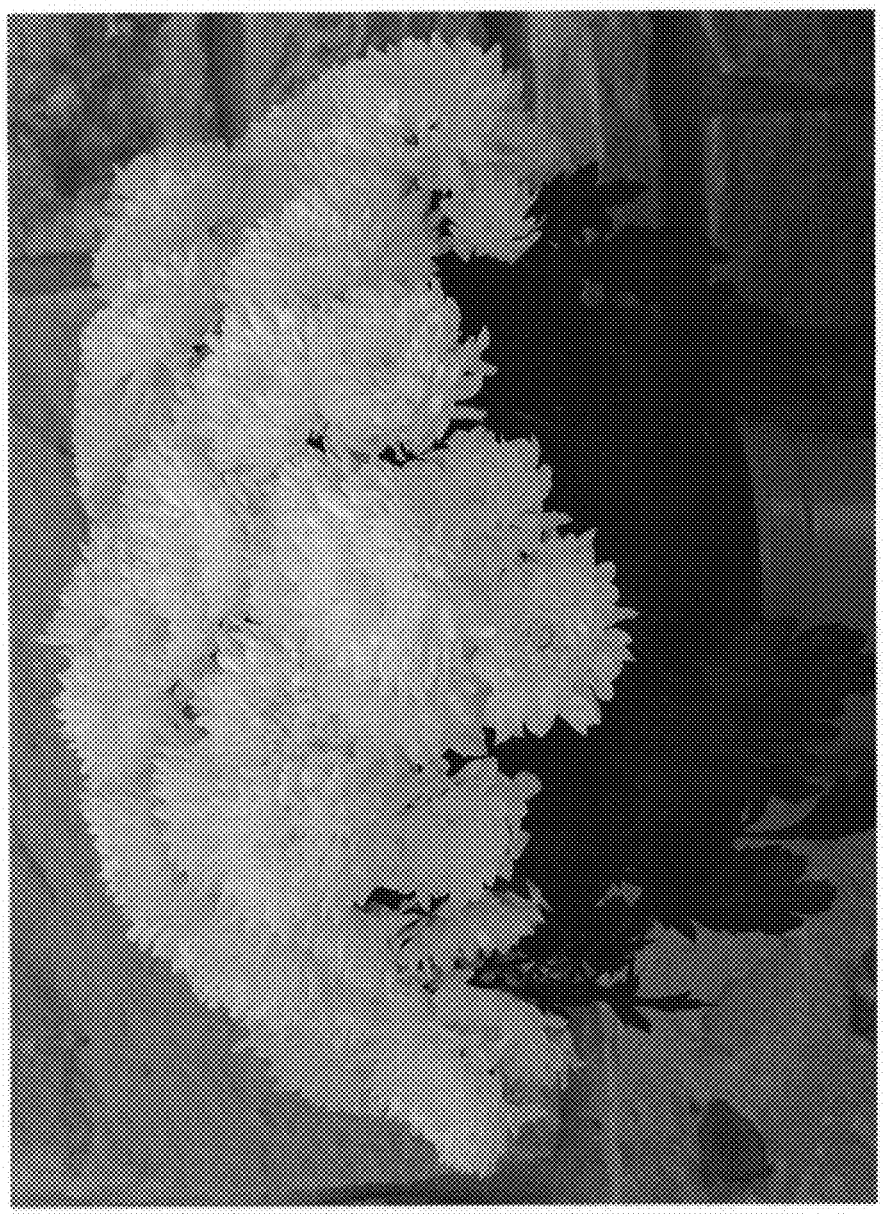

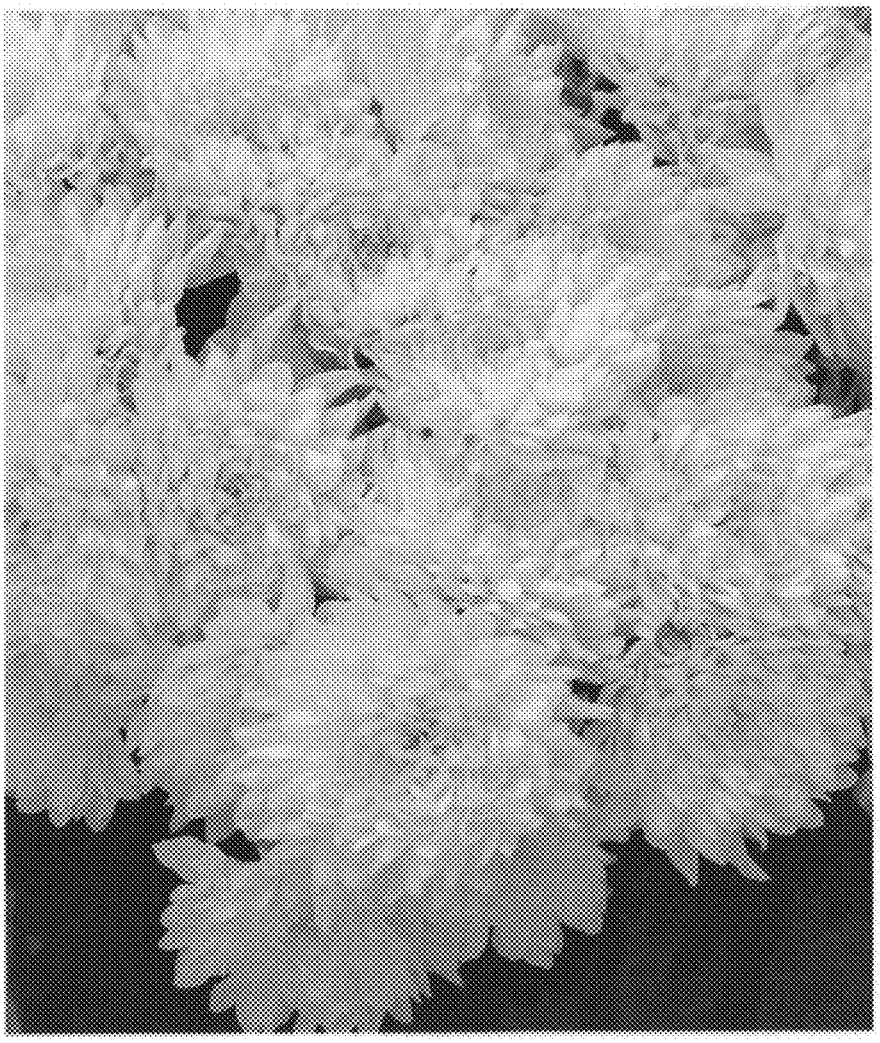

* * * * *